US009618461B2

(12) United States Patent
Ohara et al.

(10) Patent No.: US 9,618,461 B2
(45) Date of Patent: Apr. 11, 2017

(54) X-RAY ANALYSIS APPARATUS

(71) Applicant: Rigaku Corporation, Akishima-shi (JP)

(72) Inventors: Takao Ohara, Ome (JP); Kenji Wakasaya, Akishima (JP); Tetsuya Ozawa, Hino (JP); Kunio Nishi, Hachioji (JP)

(73) Assignee: RIGAKU CORPORATION, Akishima-Shi, Tokyo (JP)

( * ) Notice: Subject to any disclaimer, the term of this patent is extended or adjusted under 35 U.S.C. 154(b) by 363 days.

(21) Appl. No.: 14/050,676

(22) Filed: Oct. 10, 2013

(65) Prior Publication Data

US 2014/0105368 A1  Apr. 17, 2014

(30) Foreign Application Priority Data

Oct. 11, 2012 (JP) ................. 2012-225851

(51) Int. Cl.
*G01N 23/20* (2006.01)
*G01T 7/00* (2006.01)

(52) U.S. Cl.
CPC ......... *G01N 23/20008* (2013.01); *G01T 7/00* (2013.01); *G01N 2223/30* (2013.01); *G01N 2223/308* (2013.01)

(58) Field of Classification Search
CPC .......... A61B 2019/44; A61B 2019/442; A61B 2019/444; A61B 2019/446; A61B 2019/448; A61N 5/1048; G01T 7/00; G01N 23/20008; G01N 2223/308
See application file for complete search history.

(56) References Cited

U.S. PATENT DOCUMENTS

| | | | |
|---|---|---|---|
| 4,613,942 A * | 9/1986 | Chen ..................... | G06T 1/0014 235/375 |
| 2003/0194056 A1* | 10/2003 | Spahn ..................... | A61B 6/08 378/205 |
| 2008/0056452 A1* | 3/2008 | Sasaki .................. | G01N 23/207 378/204 |
| 2008/0230608 A1* | 9/2008 | Lallemang ............ | G06K 17/00 235/439 |
| 2008/0285724 A1* | 11/2008 | Dehler .................... | A61B 6/12 378/205 |

(Continued)

FOREIGN PATENT DOCUMENTS

| | | |
|---|---|---|
| DE | 10352556 A1 | 6/2005 |
| DE | 102007021185 A1 | 11/2008 |

(Continued)

*Primary Examiner* — Glen Kao
*Assistant Examiner* — Chih-Cheng Kao
(74) *Attorney, Agent, or Firm* — Buchanan Ingersoll & Rooney PC

(57) ABSTRACT

An X-ray analysis apparatus for detecting, using an X-ray detector, X-rays given off by a sample when the sample is irradiated with X-rays, the X-ray analysis apparatus having replaceable components. The X-ray analysis apparatus comprises labels attached to the replaceable components and including symbols indicating the types of replaceable components, a camera for photographing the replaceable components and the labels, and CPU and image recognition software for specifying the types of replaceable components by calculation based on the symbols in the labels.

10 Claims, 9 Drawing Sheets

(56) References Cited

U.S. PATENT DOCUMENTS

2010/0107499 A1* 5/2010 Kuhnmuench ......... E05D 15/48
　　　　　　　　　　　　　　　　　　　　49/260
2010/0327060 A1* 12/2010 Moran ................. G06K 7/0004
　　　　　　　　　　　　　　　　　　　　235/440

FOREIGN PATENT DOCUMENTS

| JP | 2-69750 U | 5/1990 |
| JP | H02-219000 A | 8/1990 |
| JP | 2000-275196 A | 6/2000 |
| JP | 2005-086092 A | 3/2005 |
| JP | 2008-57989 A | 3/2008 |
| JP | 2012-053857 A | 3/2012 |
| JP | 2012-156240 A | 8/2012 |
| WO | 2005/044378 A1 | 5/2005 |

* cited by examiner

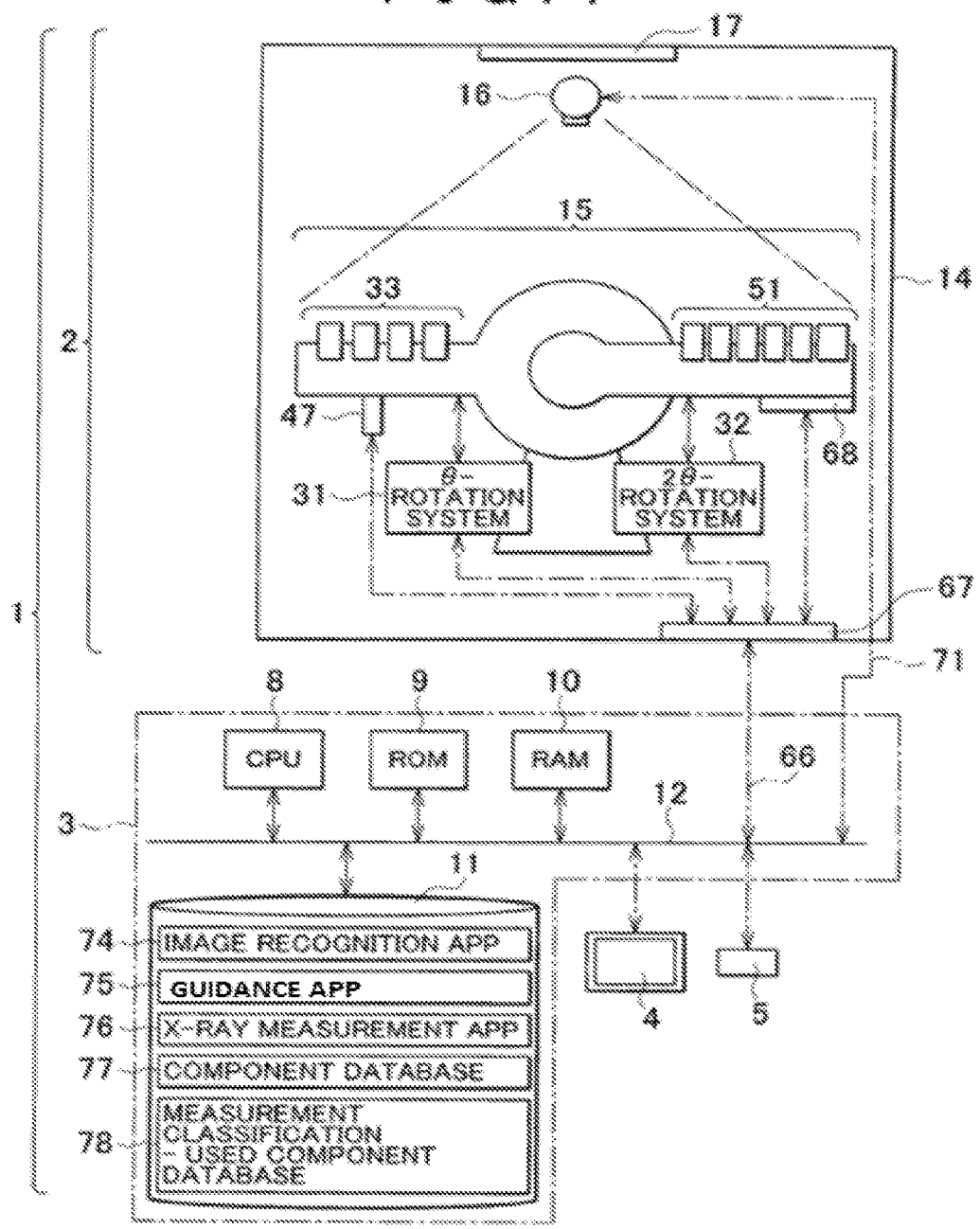

20b    20c
   20a

FIG. 5A
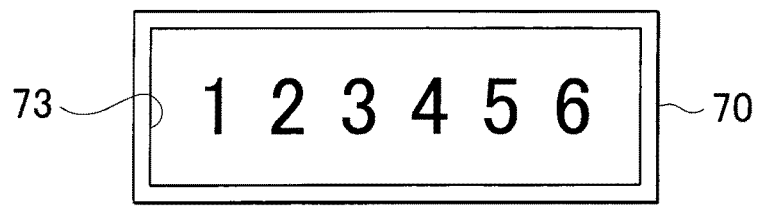
FIG. 5B
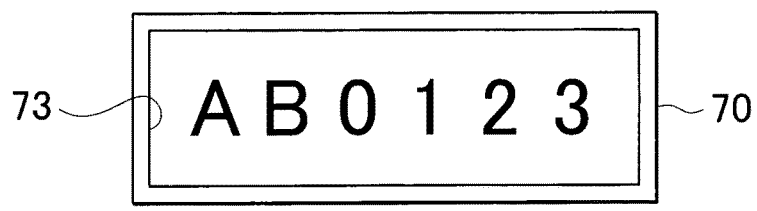
FIG. 5C
| 0 | 1 | 2 | 3 | 4 | 5 | 6 | 7 |
|---|---|---|---|---|---|---|---|
| 8 | 9 | A | B | C | D | E | F |
| G | H | I | J | K | L | M | N |
| O | P | Q | R | S | T | U | V |
| W | X | Y | Z |   |   |   |   |

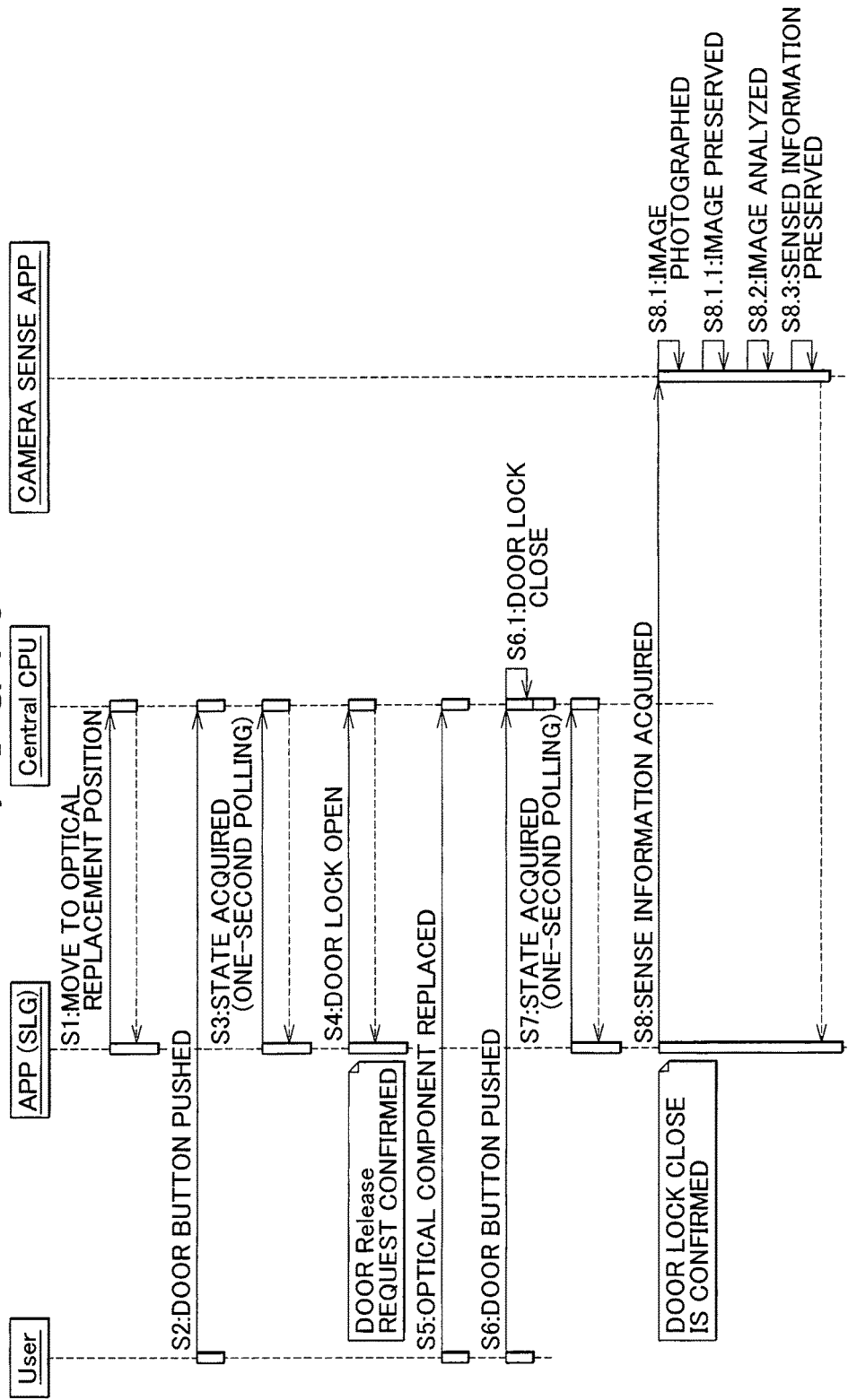

X-RAY ANALYSIS APPARATUS

BACKGROUND OF THE INVENTION

Field of the Invention

The present invention relates to an X-ray analysis apparatus for analyzing a sample using X-rays. Particularly, the present invention relates to an X-ray analysis apparatus comprising replaceable components.

Description of the Related Art

An X-ray analysis apparatus commonly has replaceable components. Examples of replaceable components include X-ray tubes, X-ray detectors, X-ray optical components, attachments (accessory devices), and the like. Examples of X-ray optical components include a slit, a monochromator, a Soller slit, a parallel slit collimator (PSC), a filter, a parallel slit analyzer (PSA), and the like. Examples of attachments include a sample holder in which the sample is filled, a sample plate unit on which the sample holder is placed, a sample changer (a sample replacement device), and various other accessory devices.

Conventionally, there are known X-ray analysis apparatuses in which a magnetic sensor is used to identify the type of X-ray tube as a replaceable component (see Patent Citation 1, for example). Also known are X-ray analysis apparatuses in which the type of slit, monochromator, filter, or other such replaceable component is identified using a photo sensor, a microswitch, or the like (see Patent Citation 2, for example).

PRIOR ART DOCUMENTS (Patent Citation 1): Japanese Utility Model Application Laid-Open Publication No. H2-069750
(Patent Citation 2): Japanese Patent Application Laid-Open Publication 2008-057989

However, in a conventional component recognition method using a sensor, a microswitch, or the like, the number of indicators for sensing are limited. For example, it has been possible to prepare only IDs (identification codes) of at most 5 bits (32 types). Therefore, one problem has been that IDs for identification have not been allocated to components exceeding the limited number.

In a conventional component recognition method using a sensor, a microswitch, or the like, a component to be inspected must be connected to a circuit board by a communication line. Therefore, the location where the component is mounted (i.e., the position of the component) is limited to a specified location, and it has not been possible to add mounting locations.

Although it has been possible to identify the type of component in a conventional component recognition method using a sensor, a microswitch, or the like, it has not been possible to recognize the mounting position of the component. It has also not been possible to recognize mounting directions, whether the component is being mounted in a longitudinal direction or mounted in a transverse direction.

SUMMARY OF THE INVENTION

The present invention was devised in view of the problems described above, and an object thereof is to provide an X-ray analysis apparatus whereby the types of recognizable components can be increased, components mounted in new mounting locations can be additionally recognized, and the mounting positions and mounting directions of the components can be recognized.

The first X-ray analysis apparatus according to the present invention is an X-ray analysis apparatus for detecting, using an X-ray detector, X-rays given off by a sample when the sample is irradiated with X-rays, the X-ray analysis apparatus comprising a replaceable component, the X-ray analysis apparatus also having an indicator provided on the replaceable component, a camera for photographing the replaceable component and the indicator, and component type calculation means for specifying the type names of the replaceable component by calculation based on an image of the indicator. The component type calculation means can be realized using a combination of a CPU and image recognition application software, for example.

With the first X-ray analysis apparatus according to the present invention, it is not that the types of component are classified using a photo sensor or the like for transmitting signals through a communication line; rather, it is that the types of optical components or the like are recognized by analyzing the images obtained by the camera photographing the indicators added to the optical components or attachments. Therefore, more types of components can be recognized by appropriately determining the indicators.

Because sensors and communication cables are not used, not only can special positions stipulated by the communication cables be recognized, but components mounted in new mounting locations can be easily recognized as well.

A conventional recognition method requires photo sensors and communication cables, but in the present embodiment, sensors and communication cables extending from the sensors are not needed because the images photographed by the camera are read and the information is converted to data. Therefore, component costs can be reduced.

In a conventional X-ray analysis apparatus, an observation window composed of lead glass is provided to an appropriate location in an opening/closing door in order to confirm the working conditions of the system, but in the X-ray analysis apparatus of the present invention, such a window is not needed and costs can be reduced because the system is photographed by a camera.

The second X-ray analysis apparatus according to the present invention is an X-ray analysis apparatus for detecting, using an X-ray detector, X-rays given off by a sample when the sample is irradiated with X-rays, the X-ray analysis apparatus comprising a replaceable component, the X-ray analysis apparatus also having an indicator provided on the replaceable component, a camera for photographing the replaceable component and the indicator, and component position calculation means for specifying the position where the replaceable component is mounted by calculation based on an image of the indicator photographed by the camera. The component position calculation means can be realized using a combination of a CPU and image recognition application software, for example.

With the second X-ray analysis apparatus according to the present invention, the positions of the replaceable components, e.g., optical components and attachments can also be recognized by including information of the positions where the replaceable components are to be mounted in the indicators.

In a conventional X-ray analysis apparatus, an observation window composed of lead glass is provided to an appropriate location in an opening/closing door in order to confirm the working conditions of the system, but in the X-ray analysis apparatus of the present invention, such a window is not needed and costs can be reduced because the system is photographed by a camera.

In the X-ray analysis apparatus according to present invention, the indicators can be either (1) a symbol added to the labels attached to the replaceable component, (2) the shape of the replaceable component, (3) a color added to the replaceable component, (4) the color of the label attached to the replaceable component, (5) a symbol written directly on the replaceable component, or (6) a symbol written directly by engraving on the replaceable component.

The labels means a generic notices which include stickers attached to components, tags attached to components, printed matters attached to components, etc. The labels display the necessary indicators. There are various methods for attaching the labels to the components, examples of which include pasting, stitching, printing directly on the components, printing directly by baking on the components, and the like.

In the X-ray analysis apparatus according to the present invention, the replaceable component can be, for example, an X-ray optical component or an attachment. The X-ray optical component may be a slit, a monochromator, or the like. The attachment may be a sample holder, or the like.

The X-ray analysis apparatus according to the present invention can further have a pattern in which two mutually orthogonal directions can be classified, and component direction calculation means for specifying the directions of the replaceable component by calculation based on the pattern. The component direction calculation means can be realized using a combination of a CPU and image recognition application software, for example.

In the X-ray analysis apparatus according to the present invention, the pattern in which two mutually orthogonal directions can be classified may be a shape of rectangular frame.

The X-ray analysis apparatus according to the present invention can have component distance calculation means for calculating the distance from a reference point in the photographed image of the camera to a specific point of the replaceable component. The component distance calculation means can be realized using a combination of a CPU and image recognition application software, for example.

The previously described "reference point in the photographed image of the camera" can be any desired point in the photographed image. For example, the reference point can be a sample center, which is the center of the area exposed to X-rays in the sample, or a specific point on a Z stage which is an attachment for adjusting the up-down position of the sample. When the reference point is a specific point on the Z stage, a label can be pasted to the desired position on the Z stage and a specific point set within the label can be the specific point of the Z stage.

In the X-ray analysis apparatus according to the present invention, a rectangular frame can be added to the replaceable component, and the specific point on the replaceable component can be a point of intersection of the diagonals of the rectangular frame. With this configuration, the specific points of the replaceable components can easily be specified. The method of determining the specific points can be a method of using the intersecting point of the diagonals, or any other desired determination method. For example, a corner of the rectangular frame may be used as the specific point, or the specific points may be determined based on shapes other than a rectangle.

In the X-ray analysis apparatus according to the present invention, the replaceable component can have an indicator having a linear length or an indicator having a planar width.

The X-ray analysis apparatus can have component Z-position calculation means for calculating a change in the length of an indicator having a linear length or a change in the area of an indicator having a planar width, and finding a change in the forward-backward position of the replaceable component relative to the camera by calculation based on the change in length or the change in area. The component Z-position calculation means can be realized using a combination of a CPU and image recognition application software, for example.

Next, the X-ray analysis apparatus according to the present invention is characterized in having calculation means for determining whether or not the replaceable component has been set to the proper state on the basis of the calculation result of at least one of the above-described component type calculation means, component position calculation means, component direction calculation means, component distance calculation means, and component Z-position calculation means.

Effects of Invention

With the first X-ray analysis apparatus according to the present invention, it is not that the types of component are classified using a photo sensor or the like for transmitting signals through a communication line; rather, it is that the types of optical components or the like are recognized by analyzing the images obtained by the camera photographing the indicators added to the optical components or attachments. Therefore, more types of components can be recognized by appropriately determining the indicators.

Because sensors and communication cables extending from the sensors are not used, not only can special positions stipulated by the communication cables be recognized, but components mounted in new mounting locations can be easily recognized as well.

A conventional recognition method requires photo sensors and communication cables, but in the present invention, sensors and communication cables extending from the sensors are not needed because the images photographed by the camera are read and the information is converted to data. Therefore, component costs can be reduced.

In a conventional X-ray analysis apparatus, an observation window composed of lead glass is provided to an appropriate location in an opening/closing door in order to confirm the working conditions of the system, but in the X-ray analysis apparatus of the present invention, such a window is not needed and costs can be reduced because the system is photographed by a camera.

With the second X-ray analysis apparatus according to the present invention, the positions of the replaceable components, e.g., optical components and attachments can also be recognized by including information of the positions where the replaceable components are to be mounted in the indicators.

In a conventional X-ray analysis apparatus, an observation window composed of lead glass is provided to an appropriate location in an opening/closing door in order to confirm the working conditions of the system, but in the X-ray analysis apparatus of the present invention, such a window is not needed and costs can be reduced because the system is photographed by a camera.

BRIEF DESCRIPTION OF THE DRAWINGS

FIG. 1 is a diagram showing the mechanical and electrical configuration of an embodiment of an X-ray analysis apparatus according to the present invention;

FIG. 5A is a diagram showing an example of a label as an important component of the X-ray analysis apparatus of the present invention;

FIG. 5B is a diagram showing another example of a label;

FIG. 5C is a diagram showing an example of symbols attached to the label;

FIG. 6 is a sequence chart showing part of the action of the X-ray analysis apparatus of FIG. 1;

DESCRIPTION OF THE PREFERRED EMBODIMENTS

First Embodiment of X-Ray Analysis Apparatus

Figure 2A:
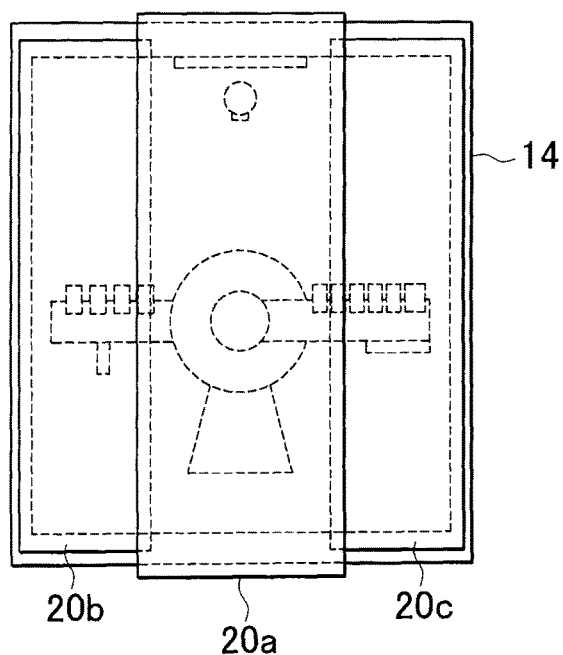
FIG. 2A is a drawing showing the closed state of the doors of the case enclosing the X-ray measurement system, which is a mechanical configurational element of the X-ray analysis apparatus of FIG. 1.

The X-ray analysis apparatus according to the present invention will now be described below based on the embodiments. It should be noted that the present invention is not limited to the following embodiment. In the drawings accompanying the specification, the configurational elements may be illustrated with different ratios from the actual element in order to make characteristic portions easier to understand.

FIG. 1 shows an embodiment of an X-ray analysis apparatus according to the present invention. In FIG. 1, an X-ray analysis apparatus 1 of the present embodiment has an X-ray measurement system 2, a control device 3, a display device 4, and an input device 5. In the X-ray measurement system 2, when a sample is irradiated with X-rays, the X-rays exiting the sample; e.g., diffracted X-rays, are detected by an X-ray detector.

The control device 3 is a device for controlling the actions of the X-ray measurement system 2, and processing the measurement data obtained by the X-ray measurement system 2. The display device 4 is a device for displaying various data as images on a screen, e.g., a flat display panel known as a liquid crystal display device or the like. The input device 5 is a device used when an operator inputs data to the control device 3, and is a keyboard, a mouse, or the like, for example.

In the present embodiment, the control device 3 is configured by a computer system in which a central processing unit (CPU) 8, a read only memory (ROM) 9, a random access memory (RAM) 10, and a memory 11 are connected to a bus 12. The display device 4 and the input device 5 are connected to the CPU 8 via a suitable interface.

(X-Ray Measurement System)

The X-ray measurement system 2 has an X-ray shield case 14 capable of blocking X-rays, a measurement operating system 15 installed inside the shield case 14, a camera 16 installed in a position near the ceiling of the shield case 14, and an illumination device, e.g., a light emitting diode (LED) illumination device 17 provided to the ceiling of the shield case 14. The camera 16 is a camera having a function for specifying positions in a photographed image as coordinate values among two-dimensional coordinates. Such a camera can be configured using a typical charge coupled device (CCD) camera, a so-called WEB camera, or the like.

During measurement, the front open surface of the X-ray shield case 14 is closed by a middle door 20a and left and right doors 20b, 20c, as shown in FIG. 2A. When an operator performs an operation necessary for the measurement operating system 15, the middle door 20a and the left and right doors 20b, 20c are slid to the left and right and the front open surface of the X-ray shield case 14 is widely opened to the exterior. A combination of the case 14 and the doors 20a, 20b, 20c forms a cover for enclosing the measurement operating system 15.

Figure 3:
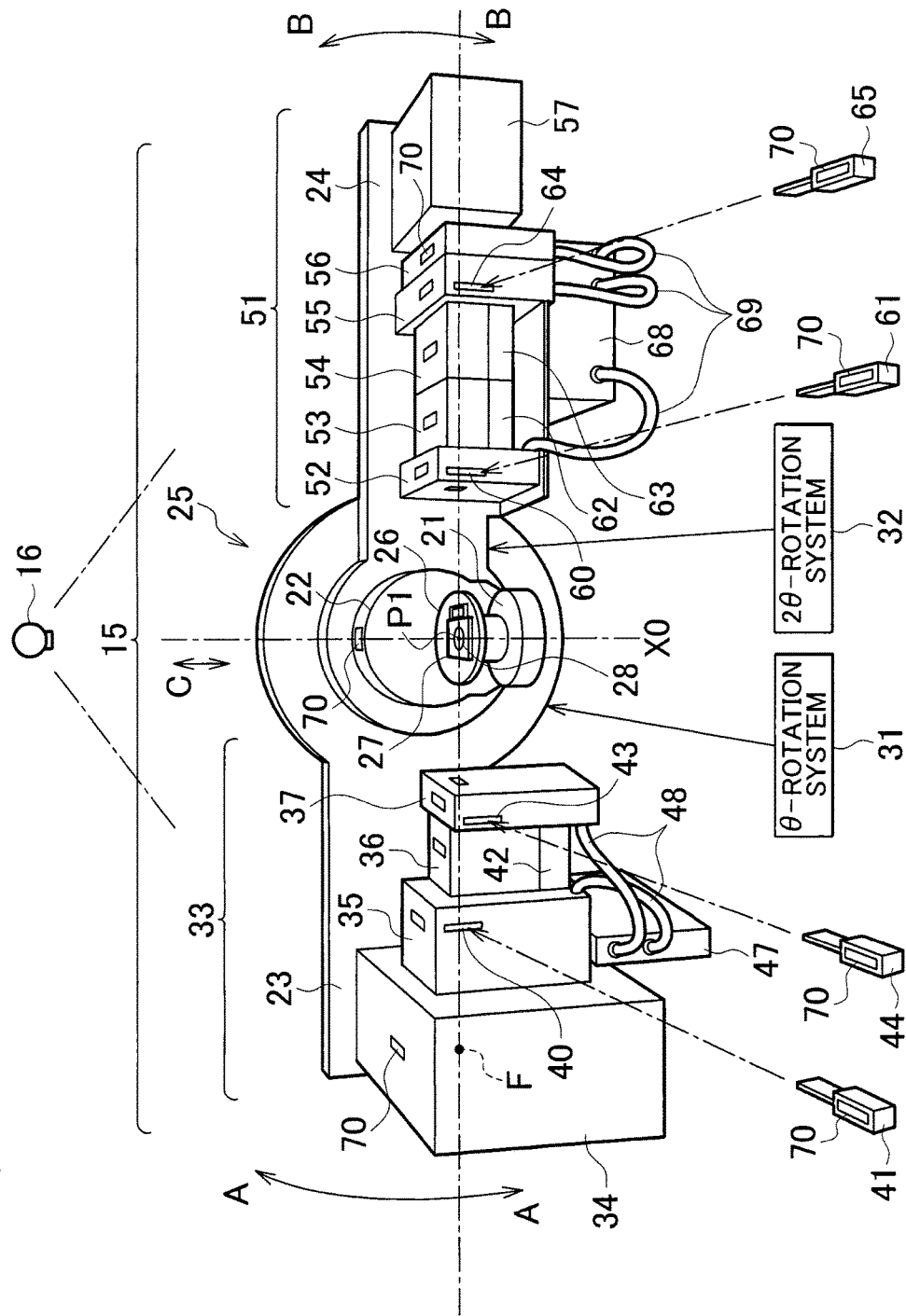
FIG. 3 is a drawing showing a measurement operating system which is a mechanical configurational element of the X-ray analysis apparatus of FIG. 1.
Figure 4:
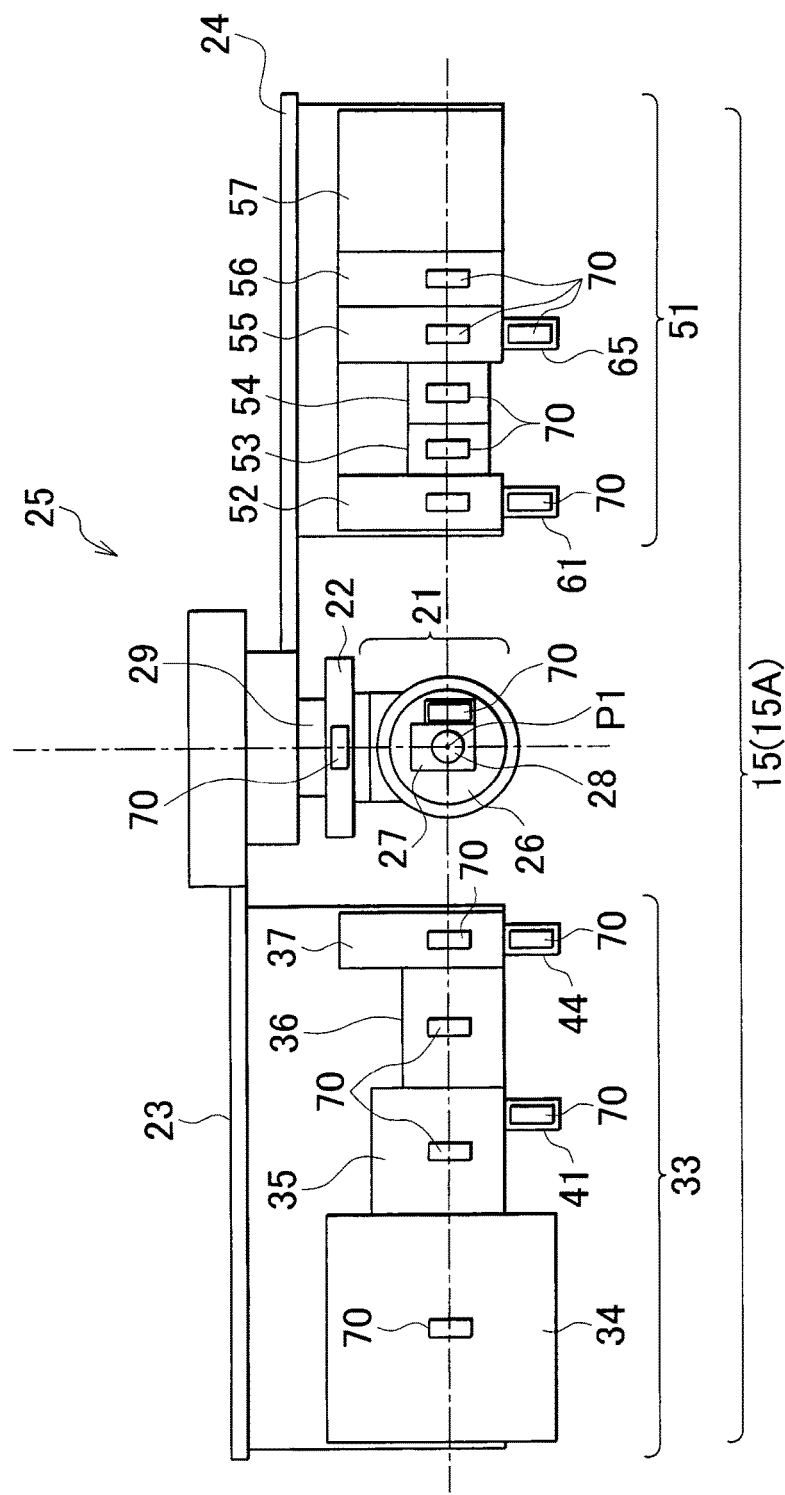
FIG. 4 is a plan view of the measurement operating system of FIG. 3.

The measurement operating system 15 has a goniometer 25 having an incident arm 23 and a receiving arm 24, as shown in FIGS. 3 and 4. A Z-axis stage 22 is mounted in the center portion of the goniometer 25. A sample stage 21 is mounted on the Z-axis stage 22. A sample plate 26 is mounted on this sample stage 21. A sample 28 as the object of measurement is filled into a sample holder 27. This sample holder 27 is placed on top of the sample plate 26. The Z-axis stage 22, the sample stage 21, the sample plate 26, and the sample holder 27 each constitute one attachment.

A vertical drive device 29 (see FIG. 4) is appended to the Z-axis stage 22. The Z-axis stage 22 is moved vertically (as shown by the arrow C in FIG. 3, the direction perpendicular to the image plane in FIG. 4) by the vertical drive device 29, whereby the vertical position of the sample 28 can be adjusted. In other words, the Z-axis stage 22 functions as a sample vertical position adjuster for making adjustments to the vertical position of the sample 28.

In the present embodiment, the Z-axis stage 22, the sample stage 21, the sample plate 26, and the sample holder 27 are exemplified as attachments. However, there are various other attachments in addition to these. Other examples of attachments include a sample changer, a sample oscillation mechanism, and the like.

A θ-rotation system 31 is connected to the incident arm 23. A 2θ-rotation system 32 is connected to the receiving arm 24. The incident arm 23 is driven by the θ-rotation system 31 to undergo a rotating motion about a sample center line X0, which is a horizontal line passing through the surface of the sample 28, as shown by the arrow A-A. The receiving arm 24 is driven by the 2θ-rotation system 32 to undergo a rotating motion about the sample center line X0 as shown by the arrow B-B.

The θ-rotation system 31 and the 2θ-rotation system 32 can be configured by rotation drive structures having any desired structure. The present embodiment employs a rotation system wherein a motor in which rotational angle can be controlled, e.g., a servo motor, a pulse motor, or the like is used as the power source, and the power is transmitted to the arms via a power transmission system composed of a worm and a worm wheel.

(Incident Optical System)

The incident arm 23 supports an incident optical system 33. The incident optical system 33 has an X-ray tube 34, a cross beam optics (CBO) unit 35, an incidence-side first optical element 36, and an incidence slit box 37. Inside the X-ray tube 34 is an X-ray focal point F as an X-ray source.

(CBO Unit)

The CBO unit 35 is a unit for forming X-rays of a strength and cross-sectional shape corresponding to respective classifications of measurement (for example, powder measurement, small-angle scattering measurement, microscopic measurement, in-plane measurement, and the like). The CBO unit 35 has a multilayer mirror in the interior. A motor for adjusting the position of the multilayer mirror is housed inside the CBO unit 35. A driver for controlling the rotation of the output shaft of this motor is housed inside an interface board 47. The motor and the driver in the board 47 are connected by a communication cable 48, which is a communication line.

The CBO unit 35 has a slit insertion hole 40. A selection slit 41 can be inserted into this slit insertion hole 40. The inserted selection slit 41 is positioned on the X-ray outgoing side of the multilayer mirror.

The following four types of slits are possible examples of components that can be the selection slit 41.
(1) Selection slit BB
(2) Selection slit PB
(3) Selection slit SA
(4) Selection slit MA "BB" is a slit for a focusing method, "PB" is a slit for a parallel beam method, "SA" is a slit for a small-angle scattering measurement, and "MA" is a slit for a microscopic measurement. The selection slit SA may be obtained by reducing the width of the selection slit PB. The selection slit MA may be obtained by reducing the length of the selection slit PB. A hollow block is sometimes placed in the location where the CBO unit 35, instead of the CBO unit 35. Such a hollow block is sometimes known as an incident path.

(Incidence-Side First Optical Element)

The incidence-side first optical element 36 is detachably mounted on top of an element base 42. The following examples of X-ray optical elements are applicable as the incidence-side first optical element 36.
(1) two-crystal monochromator Ge (220)×2
(2) two-crystal monochromator Ge (400)×2
(3) four-crystal monochromator Ge (220)×4
(4) four-crystal monochromator Ge (400)×4
(5) Soller slit Open
(6) Soller slit 5 deg
(7) Soller slit 2.5 deg
(8) In-plane parallel slit collimator (PSC) 1.0 deg
(9) In-plane PSC 0.5 deg
(10) In-plane PSC 0.15 deg A monochromator is mounted directly on the element base 42. A Soller slit and an in-plane PSC are mounted on the monochromator mounted on the element base 42, or are mounted on the element base 42 via a exclusive incident parallel slit (IPS) adapter.

In some cases a monochromator, a Soller slit, and a PSC are not provided to the location where the incidence-side first optical element 36 is mounted. There are also cases in which an IPS adapter is not mounted.

(Incidence Slit Box)

The incidence slit box 37 has a slit insertion hole 43. A length-restriction slit 44 can be inserted into the slit insertion hole 43. The following slits are possible examples of components that can be the length-restriction slit 44.
(1) Length-restriction slit 0.5 mm
(2) Length-restriction slit 2 mm
(3) Length-restriction slit 5 mm
(4) Length-restriction slit 10 mm
(5) Length-restriction slit 15 mm A motor for opening and closing the slit is housed inside the incidence slit box 37. A driver for controlling the rotation of the output shaft of the motor is housed in the interface board 47. The above-described motor and the driver inside the board 47 are connected by the communication cable 48, which is a communication line.

In the X-ray analysis apparatus disclosed in Patent Citation 2 (JP A 2008-057989), a method for sensing indicators by a photo sensor is employed in order to sense the type name of the first optical element 36 mounted on the element base 42 in FIG. 3 of the present application. Therefore, it has been necessary to join the element base 42 and the board 47 by a communication cable, and to output the output signals of the photo sensor on the element base 42 to the exterior through the communication cable and the board 47.

In the present embodiment, the type name of the incidence-side first optical element 36 and the position where the incidence-side first optical element 36 is to be mounted are recognized by a recognition method using a camera as is described hereinafter; therefore, there is no need to use a photo sensor or the like as a sensing element on the element base 42, and there is therefore no need to connect the element base 42 and the board 47 by the communication cable 48.

(Receiving Optical System)

In FIG. 3, the receiving arm 24 supports a receiving optical system 51. The receiving optical system 51 has a first receiving slit box 52, a receiving-side second optical element 53, a receiving-side third optical element 54, a second receiving slit box 55, an attenuator box 56, and an X-ray detector 57.

(First Receiving Slit Box)

The first receiving slit box 52 houses a receiving slit and a motor for opening and closing the slit. The first receiving slit box 52 also has a slit insertion hole 60. A Kβ filter 61 can be inserted into this slit insertion hole 60.

(Receiving-Side Second Optical Element)

The receiving-side second optical element 53 is detachably mounted on top of an ROD adapter (a receiving optical element adapter) 62. The following X-ray optical elements are applicable examples of the receiving-side second optical element 53.
(1) Parallel slit analyzer (PSA) Open
(2) PSA 1.0 deg
(3) PSA 0.5 deg
(4) PSA 0.114 deg
(5) PSA 0.05 deg
(6) Vacuum Path Sometimes a space is left open where the PSA is not mounted on top of the ROD adapter 62.

(Receiving-Side Third Optical Element 54)

The receiving-side third optical element 54 is detachably mounted on top of a receiving parallel slit adapter (RPS adapter) 63. The following X-ray optical elements are applicable examples of the receiving-side third optical element 54.
(1) Soller slit 5 deg
(2) Soller slit 2.5 deg
(3) In-plane parallel slit analyzer (PSA) 1.0 deg
(4) In-plane PSA 0.5 deg
(5) In-plane PSA 0.114 deg In some cases the RPS adapter 63 is not provided. In some cases a neither a Soller slit nor an in-plane PSA is mounted on the RPS adapter 63 and the space is left open.

(Second Receiving Slit Box)

A receiving slit is provided inside the second receiving slit box 55. Also provided inside the second receiving slit box 55 is a motor for opening and closing the slit. The second receiving slit box 55 is also provided with a slit insertion hole 64. A height limiting slit 65 can be inserted in this slit insertion hole 64. In some cases the height limiting slit 65 is not inserted in the slit insertion hole 64.

(Attenuator Box)

An attenuator is provided inside the attenuator box 56. Also provided inside the attenuator box 56 is a motor for switching the type of attenuator.

Housed in an interface board 68 are drivers for controlling the rotation of the output shafts of the respective motors in the first receiving slit box 52, the second receiving slit box 55, and the attenuator box 56. The motors in the boxes and the drivers in the board 68 are connected by a communication cable 69 which is a communication line.

In the X-ray analysis apparatus disclosed in Patent Citation 2 (JP-A 2008-057989), a method for sensing indicators by photo sensor is employed in order to sense the type of second optical element 53 mounted on the ROD adapter 62 in FIG. 3 of the present application, and also in order to sense the type of third optical element 54 mounted on the RPS adapter 63. Therefore, it has been necessary to join the ROD adapter 62 and the board 68 by a communication cable, to join the RPS adapter 63 and the board 68 by a communication cable, and to output the output signals of the photo sensors on the adapters 62, 63 to the exterior through the communication cable 69 and the board 68.

In the present embodiment, the type names of the second optical element 53 and the third optical element 54 and the positions where these elements are to be mounted are recognized by a recognition method that uses a camera as described hereinafter; therefore, there is no need to provide sensing elements, such as photo sensors, on the adapters 62, 63, and there is therefore no need to connect the adapters 62, 63 and the board 68 with the communication cable 69.

The output lines of the interface board 47, the θ-rotation system 31, the 2θ-rotation system 32, and the interface board 68 are connected to a terminal on the measurement side of a controller 67. A terminal on the control side of the controller 67 is connected to the CPU 8 of the control device 3 by a LAN cable 66. The input/output terminal of the camera 16 is connected to the CPU 8 of the control device 3 by a communication cable 71.

(Measurement Classification)

In the measurement operating system 15 of FIG. 3 in the present embodiment, various measurements can be performed by replacing components as appropriate. For example, measurement using the focusing method, measurement for reflectivity, small-angle scattering measurement, microscopic measurement, and various other types of measurements can be performed. In order to perform these measurements, one or some optical components are replaced as appropriate to constitute the optimal optical system. In cases in which measurement using the focusing method, measurement for reflectivity, and small-angle scattering measurement are performed, for example, the optical components shown in the tables below are selectively used in the measurement operating system 15 shown in FIG. 3.

(1) Measurement classification=simple wide-angle measurement (focusing method), sample=powdered sample filled in glass sample plate

|  | When adjusting Optical system | When adjusting Sample position | When measuring Data |
|---|---|---|---|
| CBO selection slit 41 | BB | BB | BB |
| First optical element 36 (crystal monochromator) | none | none | none |
| First optical element 36 (incident parallel slit) | Soller Slit 5.0 deg | Soller Slit 5.0 deg | Soller Slit 5.0 deg |
| Length-restriction slit 44 | 10 mm | 10 mm | 10 mm |
| Filter 61 | none | none | none |
| Second optical element 53 (parallel slit analyzer) | PSA open | PSA open | PSA open |
| Third optical element 54 (receiving parallel slit) | Soller Slit 5.0 deg | Soller Slit 5.0 deg | Soller Slit 5.0 deg |
| Height limiting slit 65 | none | none | none |
| Attenuator 56 | none | none | none |

(2) Measurement classification=measurement for reflectivity (high resolution), sample=thin-film sample of 1 cm×1 cm

|  | When adjusting Optical system | When adjusting Sample position | When measuring Data |
|---|---|---|---|
| CBO selection slit 41 | PB | PB | PB |
| First optical element 36 (crystal monochromator) | Ge (220) × 2 | Ge (220) × 2 | Ge (220) × 2 |
| First optical element 36 (incident parallel slit) | Soller Slit Open | Soller Slit Open | Soller Slit Open |
| Length-restriction slit 44 | 10 mm | 5 mm | 5 mm |
| Filter 61 | none | none | none |
| Second optical element 53 (parallel slit analyzer) | PSA open | PSA open | PSA open |
| Third optical element 54 (receiving parallel slit) | Soller Slit Open | Soller Slit Open | Soller Slit Open |
| Height limiting slit 65 | none | none | none |
| Attenuator 56 | none | none | none |

(3) Measurement classification=Transmitting type small-angle scattering measurement, sample=nanoparticles sealed in capillaries

|  | When adjusting Optical system | When adjusting Sample position | When measuring Data |
|---|---|---|---|
| CBO selection slit 41 | SA | SA | SA |
| First optical element 36 (crystal monochromator) | none | none | none |

-continued

| | When adjusting Optical system | When adjusting Sample position | When measuring Data |
|---|---|---|---|
| First optical element 36 (incident parallel slit) | Soller Slit 5.0 deg | Soller Slit 5.0 deg | Soller Slit 5.0 deg |
| Length-restriction slit 44 | 10 mm | 10 mm | 10 mm |
| Filter 61 | none | none | none |
| Second optical element 53 (parallel slit analyzer) | Vacuum path | Vacuum path | Vacuum path |
| Third optical element 54 (receiving parallel slit) | none | none | none |
| Height limiting slit 65 | none | none | none |
| Attenuator 56 | none | none | none |

(Configuration for Recognizing Type of Replaceable Component and Mounted Position)

As described above, in the X-ray analysis apparatus of the present embodiment, the optical components must be replaced according to the measurement classification. Replacement of the optical components is done manually by an operator in the present embodiment. When the optical components has been replaced, inspections must be made concerning whether or not the optical components are the proper type, whether or not the optical components are mounted in the proper positions, etc. When such an inspection is made, first, the type of optical component and the position where the optical component is to be mounted must be properly recognized. The following is a description of a method for recognizing the type and position of an optical component in the present embodiment.

FIG. 4 shows a plan view of the measurement operating system 15 of FIG. 3 as seen from above. This drawing is equivalent to an image of the measurement operating system 15 when the measurement operating system 15 is photographed by the camera 16 provided in the top of the shield case 14 in FIG. 1.

In FIG. 4, labels 70 are attached to the top surfaces of the X-ray tube 34, the CBO unit 35, the selection slit 41, the incidence-side first optical element 36, the incidence slit box 37, and the length-restriction slit 44, in the incident optical system 33. Whereas the method for attaching the labels 70 can be any desired method, the labels are bonded by an adhesive in the present embodiment.

Labels 70 are also attached by an adhesive or the like to the top surfaces of the first receiving slit box 52, the filter 61, the receiving-side second optical element 53, the receiving-side third optical element 54, the second receiving slit box 55, the height limiting slit 65, and the attenuator box 56, in the receiving optical system 51. A label 70 is also attached to the top surface of the Z-axis stage 22 which is one attachment, and a label 70 is also attached to the top surface of the sample holder 27 which is another attachment.

Rectangular frame patterns 73 are included on the labels 70 as shown in FIGS. 5A and 5B, and included inside the frames of the patterns 73 are six numerals or alphabetic letters, i.e., identification symbols, i.e., indicators. Of these six symbols, the first two symbols on the left (i.e., "12" in FIG. 5A and "AB" in FIG. 5B) indicate the location (i.e., the position) where the component carrying the label 70 is to be mounted.

The two center symbols of the six (i.e., "34" in FIG. 5A and "01" in FIG. 5B) indicate the type name of the component carrying the label 70. These two center symbols are symbols allocated to the selection slit BB if the component is a selection slit BB, or symbols allocated to the double crystal monochromator Ge (220)×2 if the component is the double crystal monochromator Ge (220)×2, for example. Furthermore, of the six identification symbols, the two on the right end (i.e., "56" in FIG. 5A and "23" in FIG. 5B) are a checksum for detecting incorrect recognitions.

The 6-digit indicator is selected from at total of 36 symbols from 0 to 9 and from A to Z shown in FIG. 5C, excluding the five symbols "0," "1," "I," "O," and "Q." The reason these five symbols are excluded is because they are thought to have a high probability of resulting in an incorrect recognition. If there are any other symbols thought to likely result in an incorrect recognition, such symbols are preferably not used as indicators. The number of symbols used as indicators may be a number other than six, such as five, for example.

(Control Device)

In FIG. 1, the memory 11 as a configurational element of the control device 3 is formed by a storage medium of a suitable structure, e.g., a hard disk or a semiconductor memory. The storage medium itself may include one or more media. Application software 74 for image recognition, application software 75 for guidance, and application software 76 for X-ray measurement are installed, i.e., stored in the memory 11. A component database 77 and a measurement classification-used component database 78 are also stored in the memory 11.

The image recognition application software 74 is application software for analyzing images photographed by the camera 16. The guidance application software 75 is software for guiding the operator on how to advance through various types of X-ray measurements. Specifically, the guidance application software 75 is software for informing the operator what type of X-ray components and what type of attachments to use when performing a certain type of X-ray measurement. The guidance application software 75 is also software for informing the operator of the positions to place what type of X-ray components and what type of attachments to use when performing a certain type of X-ray measurement.

The X-ray measurement application software 76 is software for using the measurement operating system 15 to carry out various types of X-ray measurements, e.g., measurement using the focusing method, measurement for reflectivity, in-plane measurement, small-angle scattering measurement, microscopic measurement, and other various measurements.

The component database 77 is a database stipulating the relationship between the symbols that, of the six identification symbols attached to the label 70, correspond to the position where the component is to be mounted (the two symbols on the left end in the present embodiment) and the position where the X-ray optical component is to be mounted; as well as the relationship between the symbols corresponding to the position where the component is to be mounted and the position where the attachment is to be mounted.

The component database 77 is a database stipulating the relationship between the name of the X-ray optical component and the symbol corresponding to the component classification (the two center symbols in the present embodiment) from among the six identification symbols attached to the labels 70 in FIGS. 5A and 5B, as well as the relationship between the symbol corresponding to the component classification and the name of the attachment.

The measurement classification-used component database 78 is a database stipulating what positions the X-ray component and the attachment must be placed in, in order to carry out the various types of X-ray measurements, e.g., measurement using the focusing method, measurement for reflectivity, in-plane measurement, small-angle scattering measurement, microscopic measurement, and other various measurements.

(Detailed Specific Examples of Indicators)

To make the description easier to understand, specific examples are given below to describe the indicators allocated to the optical components and the attachments. The indicators exemplified as merely examples for making the description easier to understand, and in practice, other appropriate indicators are selected as necessary. Specific examples of indicators for the description are as follows.

Indicators for attachments that are replaceable component are as follows.

| Attachment name | Indicator |
|---|---|
| Z-axis stage | AA0121 |
| Sample holder 27 | BB0242 |

The pairs of symbols on the left ends, "AA" and "BB," indicate what position the attachment should be in relative to the goniometer 25. The proper positions "AA" and "BB" relative to the goniometer 25 are defined in advance in the application software.

The middle pairs of symbols, "01" and "02," indicate the type name of the attachment. The indicator symbols for the type name of the attachment are defined in advance in the application software.

The indicators for the first optical component group (relating to a box) that can be replaced are as follows.

| Component name | Indicator |
|---|---|
| X-ray tube 34 | CC0363 |
| CBO unit 35 | DD0484 |
| Incidence slit box 37 | EE05A5 |
| First receiving slit box 52 | FF06C6 |
| Second receiving slit box 55 | GG07E7 |
| Attenuator box 56 | HH0808 |

The two symbols on the left end, "CC," "DD," . . . indicate what position these components should be in relative to the goniometer 25. The proper positions "CC," "DD," etc., relative to the goniometer 25 are defined in advance as image data or the like in the application software.

The two symbols in the middle, "03," "04," . . . indicate the type name of each component. The correlations between the type names and the two-symbol indicators are defined in advance as a data table or the like in the application software.

The indicators for second optical component group (relating to an element) that can be replaced are as follows.
(Selection Slit 41 in CBO Unit 35)

| Component name | Indicator |
|---|---|
| Selection slit BB | 115126 |
| Selection slit PB | 115227 |

-continued

| Component name | Indicator |
|---|---|
| Selection slit SA | 115328 |
| Selection slit MA | 115429 |

The two symbols "11" on the left end indicate that these components should be placed on the location (i.e., the position) of the CBO unit 35. A condition that the two symbols "11" correspond to the CBO unit 35 is defined in advance as image data or the like in the application software.

The symbols in the middle, "51" to "54," indicate the respective component type names. The correlations between the type names and the two-symbol indicators are defined in advance as a data table or the like in the application software.

(Incidence-Side First Optical Element 36)

| Component name | Indicator |
|---|---|
| 2-crystal monochromator Ge (220) × 2 | 22554A |
| 2-crystal monochromator Ge (400) × 2 | 22564B |
| 4-crystal monochromator Ge (220) × 4 | 22574C |
| 4-crystal monochromator Ge (400) × 4 | 22584D |
| Soller slit Open | 22594E |
| Soller slit 5 deg | 226046 |
| Soller slit 2.5 deg | 226147 |
| In-plane PSC 1.0 deg | 226248 |
| In-plane PSC 0.5 deg | 226349 |
| In-plane PSC 0.15 deg | 22644A |

The two symbols "22" on the left end indicate that these components should be replaced with each other and disposed on the location (i.e., position) of the incidence-side first optical element 36. A condition that the two symbols "22" correspond to the position of the incidence-side first optical element 36 is defined in advance as image data or the like in the application software.

The middle two symbols "55" to "64" indicate the respective component type names. The correlations between the type names and the two-symbol indicators are defined in advance as a data table or the like in the application software.

(Length-Restriction Slit 44 in the Incidence Slit Box 37)

| Component name | Indicator |
|---|---|
| Length-restriction slit 0.5 mm | 33656B |
| Length-restriction slit 2 mm | 33666C |
| Length-restriction slit 5 mm | 33676D |
| Length-restriction slit 10 mm | 33686E |
| Length-restriction slit 15 mm | 33696F |

The two symbols "33" on the left end indicate that these components should be replaced with each other and disposed on the location (i.e., position) of the incidence slit box 37. A condition that the two symbols "33" correspond to the position of the incidence slit box 37 is defined in advance as image data or the like in the application software.

The middle two symbols "65" to "69" indicate the respective component type names. The correlations between the type names and the two-symbol indicators are defined in advance as a data table or the like in the application software.

(Kβ Filter 61 in First Optical Slit Box 52)

| Component name | Indicator |
|---|---|
| Kβ filter 61 | 447087 |

The two symbols "44" on the left end indicate that the Kβ filter 61 should be disposed on the location (i.e., position) of the first receiving slit box 52. A condition that the two symbols "44" correspond to the position of the first receiving slit box 52 is defined in advance as image data or the like in the application software.

The middle two symbols "70" indicate that the component is a Kβ filter. The correlation between the type name and the two-symbol indicator is defined in advance as a data table or the like in the application software.

(Receiving-Side Second Optical Element 53)

| Component name | Indicator |
|---|---|
| PSA Open | 5571A8 |
| PSA 1.0 deg | 5572A9 |
| PSA 0.5 deg | 5573AA |
| PSA 0.114 deg | 5574AB |
| PSA 0.05 deg | 5575AC |
| Vacuum Path | 5576AD |

The two symbols "55" on the left end indicate that these components should be replaced with each other and disposed on the location (i.e., position) of the receiving-side second optical element 53. A condition that the two symbols "55" correspond to the position of the receiving-side second optical element 53 is defined in advance as image data or the like in the application software.

The middle two symbols "71" to "76" indicate the respective component name types. The correlations between the type names and the two-symbol indicators are defined in advance as a data table or the like in the application software.

(Receiving-Side Third Optical Element 54)

| Component name | Indicator |
|---|---|
| Soller slit 5 deg | 6677CE |
| Soller slit 2.5 deg | 6678CF |
| In-plane PSA 1.0 deg | 6679C0 |
| In-plane PSA 0.5 deg | 6680C8 |
| In-plane PSA 0.114 deg | 6681C9 |

The two symbols "66" on the left end indicate that these components should be replaced with each other and disposed on the location (i.e., position) of the receiving-side third optical element 54. A condition that the two symbols "66" correspond to the position of the receiving-side third optical element 54 is defined in advance as image data or the like in the application software.

The middle two symbols "77" to "81" indicate the respective component name types. The correlations between the type names and the two-symbol indicators are defined in advance as a data table or the like in the application software.

(Height Limiting Slit 65 in Second Receiving Slit Box 55)

| Component name | Indicator |
|---|---|
| Height limiting slit 65 | 7782EA |

The two symbols "77" on the left end indicate that the height limiting slit 65 should be disposed on the location (i.e., position) of the second receiving slit box 55. A condition that the two symbols "77" correspond to the position of the second receiving slit box 55 is defined in advance as image data or the like in the application software.

The middle two symbols "82" indicate that this component is a height limiting slit. The correlation between the type name and the two-symbol indicator is defined in advance as a data table or the like in the application software.

(Process for Recognizing Type Name and Mounting Position of Replaceable Component)

The following is a description, using the sequence chart of FIG. 6, of the process for recognizing a replaceable component (i.e., an optical component or an attachment) mounted on the measurement operating system 15 shown in FIGS. 3 and 4.

In step S1 of FIG. 6, the CPU 8 (FIG. 1) as the calculation means moves the incident arm 23 and the receiving arm 24 of FIG. 3 to a predetermined optical replacement position. In the present embodiment, the optical replacement position is the position shown in FIGS. 3 and 4, or specifically, a position where the incident optical system 33 and the receiving optical system 51 align linearly within a horizontal plane.

Next, in step S2, the user, i.e., the operator pushes a predetermined button for opening the doors 20a, 20b, 20c in FIG. 2A, and the doors are opened. When the doors are opened, the CPU 8 locks the doors in the open state in step S4. According to the guidance application software 75 in the memory 11 of FIG. 1, the CPU 8 as necessary displays indications of the optical component and attachment needed for the measurement intended by the user on the screen of the display device 4.

According to the screen display, the user performs a replacement of the optical component and the attachment as necessary in step S5. When the replacement ends, the user pushes a button for closing the doors in step S6, and the doors are closed. When the doors have closed, the CPU 8 performs a process in step S8 for sensing the configured state of the components and attachments of the measurement operating system 15.

Specifically, in step S8.1, the incident optical system 33 and the receiving optical system 51 of the measurement operating system 15 are photographed by the camera 16 of FIG. 1. The optical components and the attachments are thereby photographed, as are the labels 70 attached thereto, as shown in FIG. 4. The CPU 8 stores this photographed image in a predetermined storage area in the memory 11 (FIG. 1) in step S8.1.1.

Next, the CPU 8 analyzes the stored image. Specifically, based on the two component classification symbols of the six identification symbols on the label 70, the CPU 8 determines what optical component and what attachment are currently mounted on the goniometer 25. Based on the two position-specifying symbols of the six identification symbols, the CPU 8 determines what position the optical component and the attachment should be mounted on. The words "what position" in this case refer to a position stipulated by an expression of what number is the component in the incident optical system 33 as seen from the center, of the goniometer 25 carrying the sample 28, or what number is the component in the receiving optical system 51 as seen from the center of the goniometer 25, for example.

Based on the type of the component and the position of the component thus determined, the CPU 8 can start up the guidance application software 75 of FIG. 1 and provide the appropriate guidance to the user.

(Process for Recognizing Mounting Direction of Replaceable Component)

The image recognition application software 74 (FIG. 1) of the present embodiment can carry out a process of certifying the mounting direction of the component, in addition to the process of certifying the type and position of the optical component described above. Specifically, in FIG. 4, for each individual optical component and individual attachment, the CPU 8 determines whether the longitudinal direction of the rectangular frames 73 of the labels 70 on the individual optical components and attachments extends left to right in FIG. 4, or extends front to back in FIG. 4 (the direction perpendicular to the left-right direction).

The CPU 8 can thereby properly and easily determine whether or not the individual optical components and individual attachments face in the proper direction. To recognize the mounting direction of the components, the patterns on the labels 70 are not limited to rectangular frames 73, and are not even limited to rectangles as long as the patterns have two mutually orthogonal classifiable directions. For example, the patterns can be elliptical, ovular (namely in a shape of rectangle with both ends rounded), or shaped otherwise.

In the meantime, point-focus X-rays (i.e., X-rays having a dotted cross-sectional shape) can be taken from one wall of the X-ray tube 34. Alternatively, line-focus X-rays (i.e., X-rays having a linear cross-sectional shape) can be taken from a wall that is at a 90° angle to the first wall. In a conventional X-ray analysis apparatus, it has been difficult to determine whether the X-ray tube 34 is emitting point-focus X-rays or line-focus X-rays. In contrast, in the present embodiment, a label 70 having a rectangular frame pattern is attached to the top surface of the X-ray tube 34, and it can be easily determined whether the X-ray tube 34 is emitting point-focus X-rays or line-focus X-rays by distinguishing whether the label 70 is oriented left-to-right (in the transverse direction) or front-to-back (in the longitudinal direction).

(Process for Recognizing Position where Replaceable Component is Installed in Terms of Distance)

In addition to the process of certifying the type and position of the optical component described above and the process of recognizing the mounting direction of the optical component described above, the image recognition application software 74 (FIG. 1) of the present embodiment has a function for calculating the distance from predetermined reference positions on the replaceable component and attachment.

Figure 7A:
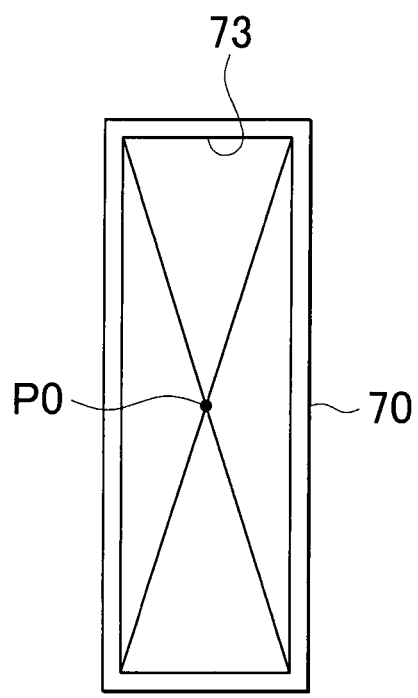
FIG. 7A is a drawing showing an example of a label (a longitudinally long label) as a main components of the X-ray analysis apparatus according to the present invention.
Figure 7B:
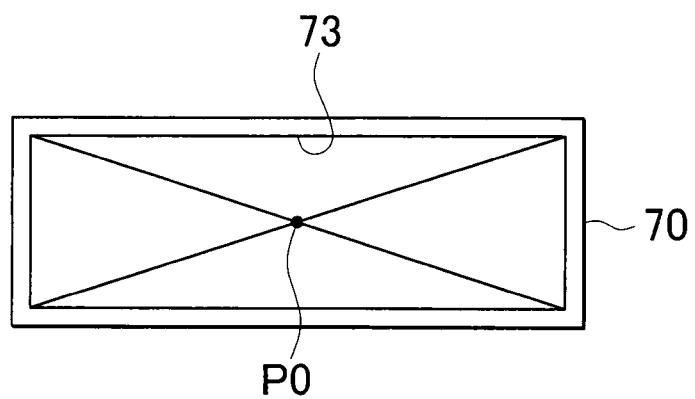
FIG. 7B is a drawing showing an example of a label (a transversely long label) as a main components of the X-ray analysis apparatus according to the present invention.

Specifically, in FIGS. 7A and 7B, the CPU 8 can recognize the intersecting point P0 of the diagonals of the rectangular frame 73 on the label 70 as the position of the label 70, and therefore as a specific point on the optical component or the attachment carrying the label 70. The CPU 8 can specify the center point P1 of the sample 28 as a reference position in FIG. 4 as image data. The CPU 8 can then find the distance between the reference position P1 and the label position P0 by calculating within the image data.

Along with the measurement data found using the X-ray analysis apparatus, the distance from the samples of the optical components is often stored as a condition for finding the measurement data. Conventionally, this distance condition has been input manually by an operator through a keyboard or the like as an input device. In contrast, in the present embodiment, the distance to the samples of the components can be found by calculating based on the image of the label 70 photographed by the camera 16, and the work of the operator can therefore be significantly reduced.

The reference position P1 is not limited to the center point of the sample 28, and can be set to any other desired position in the photographed image of the camera 16. For example, in FIG. 4, a specific point in the label 70 provided on top of the Z-stage 22 can be set as the reference point. The distance, i.e., the positions of the components relative to this reference point can then be found.

The specific point of the optical component or the attachment is not limited to only the intersecting point of the diagonals of the rectangular frame 73, and can be a corner of a rectangular workpiece 73, e.g., the upper left corner. Alternatively, the specific point can be a point within any desired shape other than a rectangle.

When the distance of the label position is sensed as described above, there are times when the incident arm 23 and the receiving arm 24 of the goniometer 25 are not in horizontal positions. In this case, the correct distance of the components can be obtained by correcting the distance found through the image taken by the camera 16 with the angle of the arm.

(Sensing Shifting in the Z-Directional Position of the Replaceable Component or Non-Replaceable Component)

In FIG. 4, the Z-axis stage 22 is provided to the center portion of the goniometer 25. This Z-axis stage 22 is driven by the vertical drive device 29 to move parallel in the vertical direction (in the direction passing through the surface of the drawing of FIG. 4) in order to adjust the vertical position of the sample 28. A label 70 is attached to the top surface of the Z-axis stage 22. A rectangular frame 73 such as the one shown in FIGS. 5A and 5B is attached to this label 70. This frame 73 functions as an indicator having linear length or an indicator having planar width. An indicator having linear length would be either a long side or a short side of the frame 73. An indicator having planar width would be the area of the region enclosed by the frame 73.

The symbol inside the frame 73 is a symbol such as "AA0121," for example, "AA" indicating the position where the Z-axis stage 22 is to be mounted, "01" indicating the type name of the Z-axis stage 22, and "21" indicating the checksum. This positional information and type name information is written in advance into the program of the application software.

The CPU 8 can calculate the lengths of the sides or the area of the frame 73 in the label 70 (see FIGS. 7A and 7B). Furthermore, by calculation, the CPU 8 can find the lengths of the sides or the area of the frame 73 at different times. If these values change over time, it can be determined that the position of the goniometer 25 has shifted vertically, i.e., in the Z direction. The CPU 8 can thereby sense the distance by which the vertical position of the Z-axis stage 22 has moved.

(Practical Example of Detected Information)

As described using FIGS. 5A and 5B, in the present embodiment, based on images obtained using the camera 16 to photograph indicators displayed on the labels 70 of the replaceable components, information indicating the type name of the component carrying the label 70 and what position the component is to be disposed in is found by the control device 3 of FIG. 1, or specifically by the CPU 8 functioning according to the image recognition application software 74.

As described using FIG. 4, in the present embodiment, a determination is made as to whether the longitudinal direction of the rectangular frames 73 of the labels 70 on the individual optical components and attachments extends left to right in FIG. 4, or front to back in FIG. 4 (the direction orthogonal to the left-right direction), and based on this determination, the direction of the components is found by the control device 3 of FIG. 1, or specifically by the CPU 8 functioning according to the image recognition application software 74.

In the present embodiment, as described using FIGS. 4, 7A, and 7B, the sample center point P1 (see FIG. 4) is selected as the reference point, the intersecting points P0 of the diagonals of the frames 73 in the labels 70 (see FIGS. 7A and 7B) on the components are selected as specific points of the components, and the distance from the specific points P0 of the components to the reference positions P1 is found by the control device 3 of FIG. 1, or specifically by the CPU 8 functioning according to the image recognition application software 74.

Furthermore, as described using FIG. 4, in the present embodiment, based on the image obtained photographing the label 70 on the Z-axis stage 22 with the camera 16, changes in the vertical position of the Z-axis stage 22 are found by the control device 3 of FIG. 1, or specifically by the CPU 8 functioning according to the image recognition application software 74.

In the control device 3 shown in FIG. 1, either the CPU 8 functioning according to the guidance application software 75, the CPU 8 functioning according to the image recognition application software 74, or the CPU 8 functioning according to the X-ray measurement application software 76 controls the multiple types of measurements (e.g., powder measurement, small-angle scattering measurement, microscopic measurement, in-plane measurement, and the like) carried out by the X-ray measurement system 2.

Stored in advance in the applications in the memory 11 or in the predetermined table data in the memory 11 is information on what types of optical components or attachments should be used corresponding to the measurement types, or information on what positions these optical components and the like should be placed in. The CPU 8 functioning as a predetermined application compares the component type name information and the component position information found from the image information obtained by the camera 16 with the data stored in the data tables and the like described above, and determines whether or not a replaceable component is the correct type of component corresponding to the measurement type, and the correct position for the component to be disposed. Further, the CPU 8 is able to determine whether the direction of the replaceable component is correct or not, based on the calculation result of the CPU 8 regarding the mounting direction of the component.

Furthermore, stored in advance in the applications in the memory 11 or the predetermined table data in the memory 11 is information on how far of a distance (in millimeters) the optical components or attachments used for the measurement types must be placed from the reference position, and information on what position in the Z-direction (i.e., vertically) the optical components or attachments used for the measurement types must be placed.

The CPU 8 functioning according to a predetermined application compares information of the "distance from the reference position" found from the image information obtained by the camera 16 with the data stored in the data table or the like described above, and determines whether or not the replaceable component is placed in the correct position corresponding to the measurement type. Furthermore, the CPU 8 functioning according to a predetermined application compares information of the "Z-directional positions of the components" found from the image information obtained by the camera 16 with the data stored in the data table or the like described above, and determines whether or not the replaceable component is placed in the correct Z-directional position corresponding to the measurement type.

As described above, the CPU 8 of the present embodiment determines whether or not a replaceable component is set (i.e., placed) in the proper state corresponding to the measurement type, by comparing the data stored in the memory 11 and the information obtained by the photographing by the camera 16.

(Effects Brought about by Present Embodiment)

As described above, according to the present embodiment, because the type of optical component or the like is recognized by analyzing the image obtained from using the camera to photograph the indicator in the label on the optical component or the attachment rather than classifying the type of component using a photo sensor or the like for transmitting signals through a communication line, more types of components can be recognized by appropriately determining the indicator on the label.

Because a sensor and a communication cable extending from the sensor are not used in order to recognize the type name of the component or the position where the component is to be mounted, not only can a special position stipulated by the communication cable be easily recognized, but a component mounted in a new mounting location can be easily recognized as well.

According to the present embodiment, because information on the position where the component is to be mounted is included in the indicator on the label, not only can the type name of the optical component or the attachment be recognized, but the position of the optical component or the like can also be recognized.

According to the present embodiment, the mounting direction of the optical component or the attachment can be recognized by including a pattern that has two recognizable directions, such as the rectangular frame 73, on the label and photographing the pattern with a camera. The indicator for recognizing the mounting direction is not limited to the rectangular frame 73, and any desired shape can be used as long as the position of the indicator can be recognized in two directions. For example, the indicator can be a triangle, any polygon other than a triangle or a square, or the like.

Conventional recognition methods have required photo sensors and communication cables, but in the present embodiment, a sensor and a communication cable extending from a sensor are not needed because the image photographed by the camera is read and the information is converted to data. Therefore, component costs can be reduced.

Figure 2B:
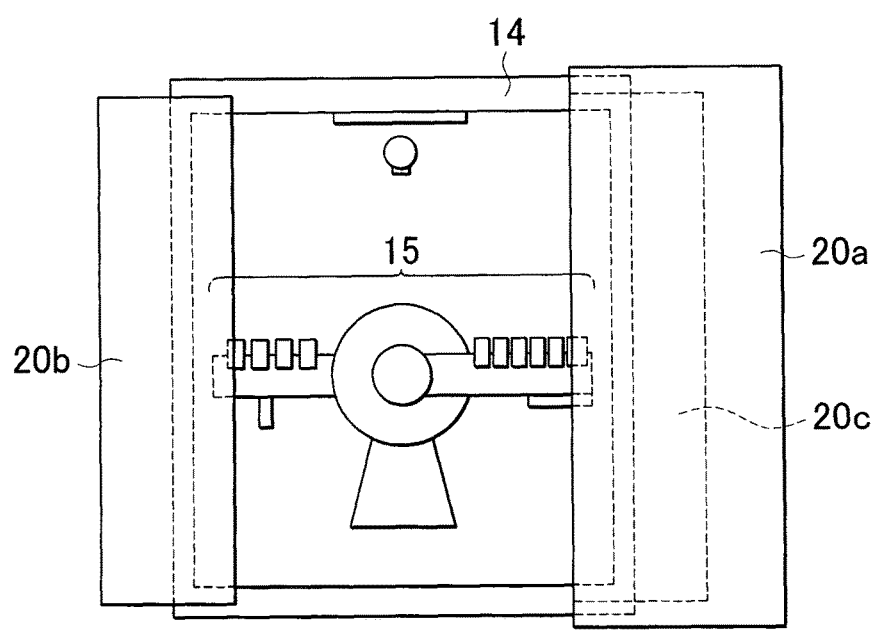
FIG. 2B is a drawing showing the opened state of the doors.

In a conventional X-ray analysis apparatus, a substance for blocking X-rays, e.g., glass containing lead is provided as an observation window to proper locations in the doors 20a, 20b, 20c of FIGS. 2A and 2B in order to confirm the working conditions of the system, but in the X-ray analysis apparatus of the present embodiment, lead glass and the like are not necessary and costs can be reduced because the system is photographed by the camera. Thus, in the present embodiment, the cover for enclosing the measurement operating system 15 may be formed by the case 14 having no observation window and the doors 20a, 20b, 20c having no observation window.

The label 70 on the sample holder 27 as an attachment contributes to recognition of the type and mounted position of the sample holder 27. Different identification symbols can be allocated to each individual sample.

(Modifications)

(1) In the above embodiment, the 6-digit symbols on the label 70 include both classifying information of the component and information of the position where the component is to be mounted. Another possible option instead is to include only one of either the classifying information of the component or the information of the position where the component is to be mounted in the label 70. With this configuration, the CPU 8 (see FIG. 1) can recognize only the classification of the component or attachment, or recognize only the position where the component or the like is to be mounted, by photographing the label 70 by the camera 16.

Figure 8A:
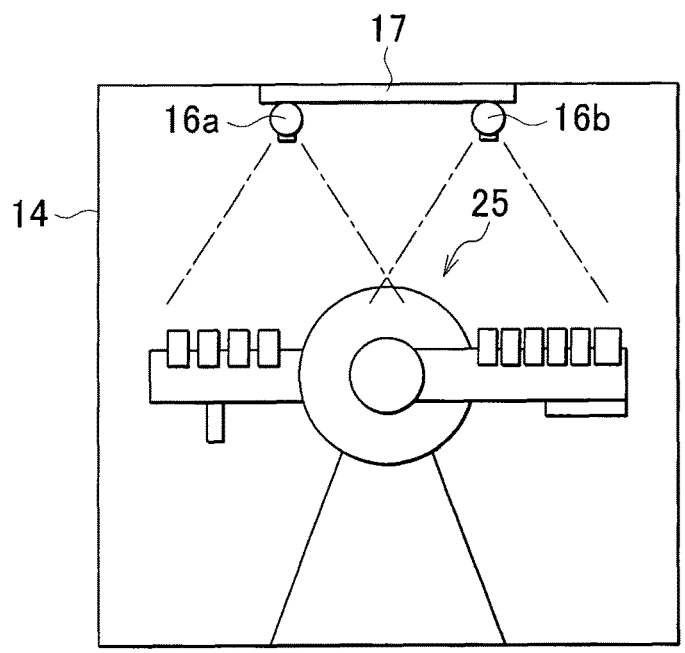
FIG. 8A is a drawing showing a modification of the X-ray analysis apparatus according to the present invention.

(2) In the above embodiment, the optical components and attachments are photographed by a single camera 16 as shown in FIG. 1. Another possible option instead, as shown in FIG. 8A, is to photograph optical components and the like using two cameras 16a and 16b. With this configuration, cameras having a narrow angle of view can be utilized.

Figure 8B:
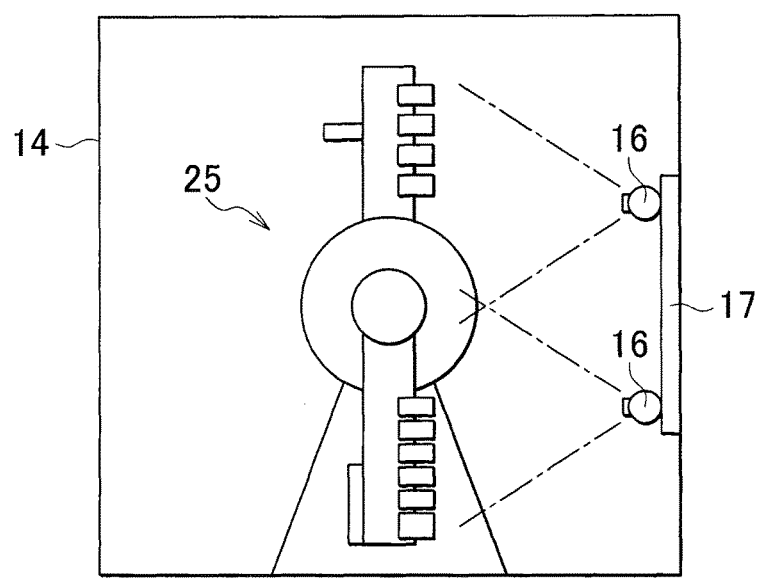
FIG. 8B is a drawing showing another modification of the X-ray analysis apparatus according to the present invention.

(3) In the above embodiment, the camera 16 is disposed in the ceiling portion of the shield case 14, and optical components and the like are photographed relative to the horizontally situated goniometer. In other words, the replacement position of the optical components and the like is set to the horizontally situated position of the goniometer. Another possible option instead, as shown in FIG. 8B, is to set up cameras 16 near the side surface wall of the shield case 14, and to set the vertical up-down situated position of the goniometer 25 to the photographed position of the optical components and the like, i.e., to the replacement position of the optical components and the like.

(4) In the above embodiment, symbols composed of numerals and letters attached to the labels 70 were used as indicators, but these can be replaced indicators such as the following:

(a) symbols attached to labels attached to the replaceable components, (b) the shapes of the replaceable components themselves, (c) the colors of the replaceable components, (d) the colors of the labels attached to the replaceable components, (e) symbols written directly on the replaceable components, and (f) symbols written directly by engraving on the replaceable components.

Second Embodiment of X-Ray Analysis Apparatus

Figure 9:
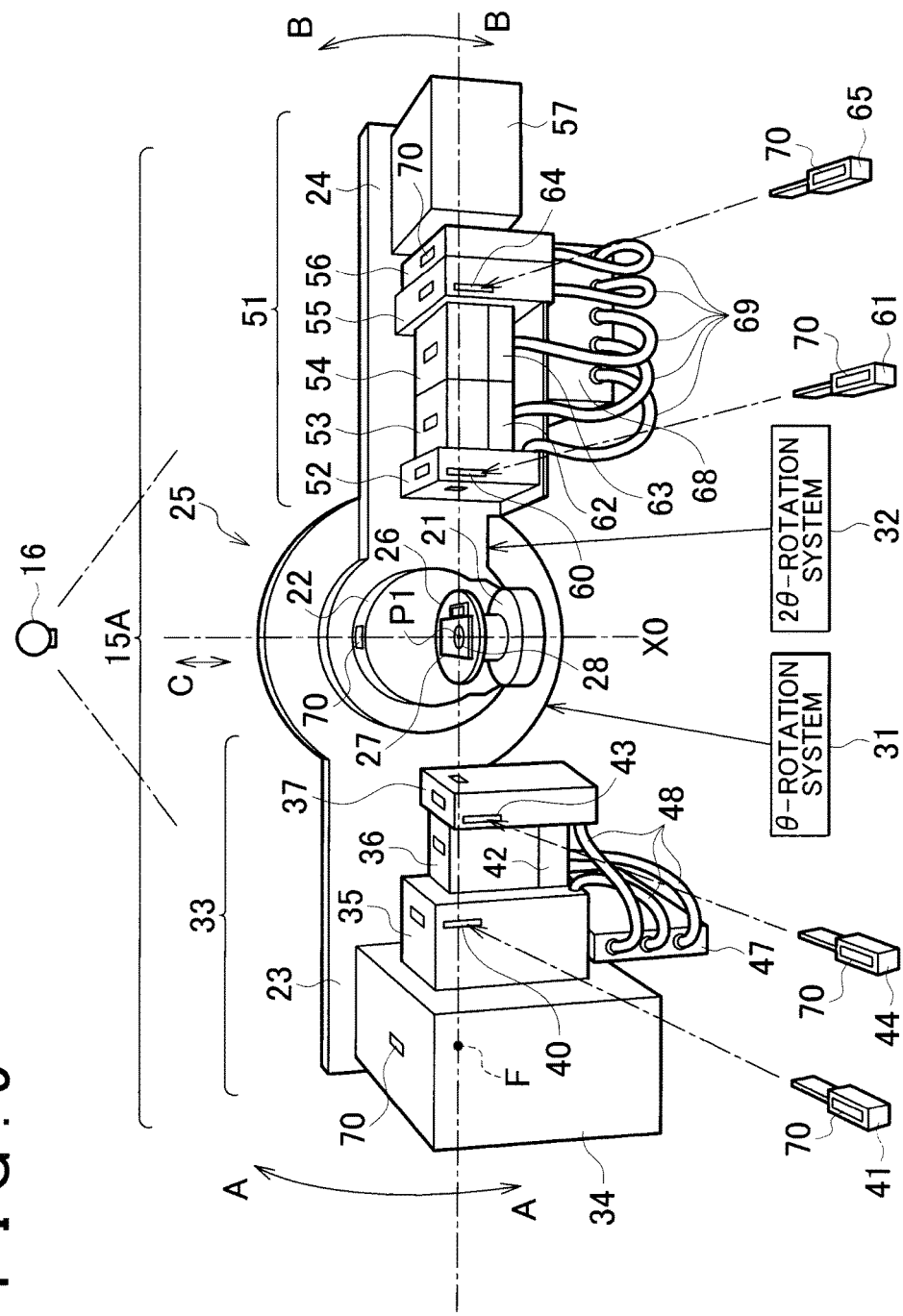
FIG. 9 is a drawing showing the measurement operating system as a main part of another embodiment of the X-ray analysis apparatus according to the present invention.

FIG. 9 shows another embodiment of the X-ray analysis apparatus according to the present invention. The overall configuration of the present embodiment is the same as the embodiment shown in FIG. 1. In the case of the present embodiment, the function carried out by the image recognition application software 74 in FIG. 1 is different from that of the first embodiment previously described.

In the first embodiment shown in FIGS. 3, 4, 5A, 5B, and 5C, the 6-digit indicators, i.e., identification symbols in the label 70 include two symbols indicating the type names of the optical components and attachments, and two symbols indicating the positions (i.e., locations) where the components or attachments are to be mounted.

In the measurement operating system 15 of FIG. 3, the elements of the replaceable components including the X-ray tube 34, the CBO unit 35, the incidence-side first optical element 36, the incidence slit box 37, the first receiving slit box 52, the receiving-side second optical element 53, the receiving-side third optical element 54, the second receiving slit box 55, and the attenuator box 56 are not provided with configurations for indicating the type names of the components (the configurations including classifying indicators, for example) and photo sensors for recognizing the configurations.

In the measurement operating system 15A of the present embodiment shown in FIG. 9, the incidence-side first optical element 36 and other optical components are given configurations for outputting the types of these components as electric signals. Such configurations include combinations of classifying indicators and photo sensors for sensing these indicators, such as the configuration disclosed in FIG. 4 of JP-A-2008-057989, for example.

Therefore, in the present embodiment, communication cables 48 extend to the interface board 47 from the optical components inside the incident optical system 33 including the CBO unit 35, the incidence-side first optical element 36, and the incidence slit box 37. And output signals of the sensors in the optical components are transmitted to the board 47 through the communication cables 48.

Communication cables 69 also extend to the interface board 68 from the optical components in the receiving optical system 51 including the first receiving slit box 52, the receiving-side second optical element 53, the receiving-side third optical element 54, the second receiving slit box 55, and the attenuator box 56. And output signals of the sensors in the optical components are transmitted to the board 68 through the communication cables 69.

Thus, in the measurement operating system 15A of the present embodiment, combinations of configurations (such as classifying indicators) for sensing the types of the replaceable components and photo sensors are employed. Therefore, in the present embodiment, symbols for indicating the type names of the optical components are not provided in the labels 70 of FIG. 4, and only symbols for indicating the positions where the replaceable components are to be mounted are provided.

Therefore, when the camera 16 of FIG. 1 is used to photograph the measurement operating system 15A of FIG. 4 to acquire image data, the labels 70 in the image data do not contain information indicating the type names of the mountable components, and only contain information indicating the positions where the components are to be mounted. Thus, in the present embodiment, information indicating the type names of the components is classified by signals outputted from the sensors housed in the components themselves, while information indicating the positions where the components are to be mounted is classified based on image information of the indicators in the labels 70 photographed by the camera 16.

According to the present embodiment, by including information of the positions where the replaceable components (i.e., the optical components and the attachments) are to be mounted in the information on the labels, not only can the components be recognized, but the positions of the components can be recognized as well.

According to the present embodiment, by attaching a pattern wherein two directions can be classified, such as the rectangular frame 73, to the label and photographing the pattern with a camera, the mounting directions of the components and attachments can be recognized.

In a conventional X-ray analysis apparatus, a substance for blocking X-rays, e.g., glass containing lead is provided as an observation window to proper locations in the doors 20a, 20b, 20c of FIGS. 2A and 2B in order to confirm the working conditions of the system. On the other hand, in the X-ray analysis apparatus of the present embodiment, lead glass and the like are not necessary and costs can be reduced because the system is photographed by the camera.

Other Embodiments

Preferred embodiments were presented to describe the present invention above, but the present invention is not limited to these embodiments; various alterations can be made within the scope of the invention as set forth in the claims.

For example, the replaceable components are not limited to components shown in FIGS. 3 and 9 including the X-ray tube 34, the CBO unit 35, the incidence-side first optical element 36, the incidence slit box 37, the first receiving slit box 52, the receiving-side second optical element 53, the receiving-side third optical element 54, the second receiving slit box 55, and the attenuator box 56, and any other desired optical components can be used as necessary.

In the above embodiments, labels 70 are added to the replaceable components, and the type names of the components and positions where the components are to be mounted are classified based on the indicators in the symbols in the labels 70. However, instead of the indicators in the labels being read, another possibility is that the types and other features of the components be classified by image recognition of the shapes of the components.

Furthermore, control can be performed so that the positions where the components are mounted are classified by image recognition of the shapes of the components, and the type names of the components are classified by the indicators in the labels.

KEY TO SYMBOLS

1. X-ray analysis apparatus, 2. X-ray measurement system, 3. control device, 4. display device, 5. input device, 11. memory, 14. X-ray shield case, 15. measurement operating system, 15A. measurement operating system, 16. camera, 17. LED illumination device, 20a. middle door, 20b, 20c. left and right doors, 21. sample stage, 22. Z-axis stage (sample up-down position adjustment part), 23. incident arm, 24. receiving arm, 25. goniometer, 26. sample plate, 27. sample holder, 28. sample, 31. θ-rotation system, 32. 2θ-rotation system, 33. incident optical system, 34. X-ray tube, 35. CBO unit, 36. incidence-side first optical element, 37. incidence slit box, 40. slit insertion hole, 41. selection slit, 42. element base, 43. slit insertion hole, 44. length-restriction slit, 47. interface board, 48. communication cable (communication line), 51. receiving optical system, 52. first receiving slit box, 53. receiving-side second optical element, 54. receiving-side third optical element, 55. second receiving slit box, 56. attenuator box, 57. X-ray detector, 60. slit insertion hole, 61. Kβ filter, 62. ROD adapter, 63. RPS adapter, 64. slit insertion hole, 65. height limiting slit, 66. LAN cable, 67. controller, 68. interface board, 69. communication cable, 70. label, 71. communication cable, 73. rectangular frame pattern, 74. image recognition application software, 75. guidance application software, 76. X-ray measurement application software, 77. component database, 78. measurement classification-used component database, X0. sample center line, A-A. θ-rotation, B-B. 2θ-rotation, F. X-ray focal point, P0. intersecting point of diagonals (specific point), P1. sample center point (reference position)

What is claimed is:

1. An X-ray analysis apparatus for detecting, using an X-ray detector, X-rays given off by a sample when the sample is irradiated with X-rays, the X-ray analysis apparatus being capable of carrying out multiple types of measurements and comprising multiple types of replaceable components, the X-ray analysis apparatus comprising:
    indicators provided on the replaceable components;
    a camera for photographing the replaceable components and the indicators;
    control means for analyzing images photographed by the camera and carrying out the various types of measurements,
    wherein:
        the indicators include information indicating type names of the replaceable components, information indicating positions where the replaceable components are mounted, and information indicating directions of the replaceable components, and
        the control means determines whether types of the replaceable components, positions of the replaceable components and directions of the replaceable components are correct or not with respect to the measurement types, based upon the information indicting type names of the replaceable components, the information indicating positions where the replaceable components are mounted, and the information indicating directions of the replaceable components photographed by the camera.

2. The X-ray analysis apparatus according to claim 1, wherein the indicator is either:
    (a) a symbol added to labels attached to the replaceable component,
    (b) the shape of the replaceable component,
    (c) a color added to the replaceable component,
    (d) a color of the label attached to the replaceable component,
    (e) a symbol written directly on the replaceable component, or
    (f) a symbol written directly by engraving on the replaceable component.

3. The X-ray analysis apparatus according to claim 1, wherein a replaceable component of the X-ray analysis apparatus is an X-ray optical component and/or an attachment.

4. The X-ray analysis apparatus according to claim 1, comprising:
    a pattern in which two mutually orthogonal directions can be classified, wherein
    the control means specifies the direction of a replaceable component of the X-ray analysis apparatus by calculation based on the pattern.

5. The X-ray analysis apparatus according to claim 4, wherein the pattern in which two mutually orthogonal directions can be classified is a rectangular frame.

6. The X-ray analysis apparatus according to claim 1, wherein the control means calculates the distance from a reference point in the photographed image of the camera to a specific point of a replaceable component of the X-ray analysis apparatus.

7. The X-ray analysis apparatus according to claim 6, wherein a rectangular frame is added to the replaceable component, and the specific point on the replaceable component is a point of intersection of the diagonals of the rectangular frame.

8. The X-ray analysis apparatus according to claim 6, wherein a rectangular frame is added to the replaceable component, and the specific point of the replaceable component is a corner of the rectangular frame.

9. The X-ray analysis apparatus according to claim 1, wherein:
- a replaceable component of the X-ray analysis apparatus has an indicator having a linear length or an indicator having a planar width, wherein
- the control means calculates a change in the length of an indicator having a linear length or a change in the area of an indicator having a planar width, and finding a change in position of the replaceable component relative to the camera by calculation based on the change in length or the change in area.

10. The X-ray analysis apparatus according to claim 1, further comprising a cover which encloses means for irradiating the sample with X-rays, the X-ray detector, the replaceable components, and the camera, wherein the cover is formed by a case having no observation window and a door having no observation window.

\* \* \* \* \*